United States Patent [19]

Oetjen et al.

[11] 4,327,717
[45] May 4, 1982

[54] HUMIDITY EXCHANGER FOR A BREATHING APPARATUS

[75] Inventors: Georg-Wilhelm Oetjen, Lübeck; Frank Benthin, Lübeck-Hamberge, both of Fed. Rep. of Germany

[73] Assignee: Drägerwerk Aktiengesellschaft, Fed. Rep. of Germany

[21] Appl. No.: 162,599

[22] Filed: Jun. 24, 1980

[30] Foreign Application Priority Data

Jul. 21, 1979 [DE] Fed. Rep. of Germany ....... 2929615

[51] Int. Cl.³ ............................................. A61M 15/00
[52] U.S. Cl. ........................... 128/201.13; 128/204.13; 261/DIG. 65; 165/140; 165/DIG. 10
[58] Field of Search ....................... 128/201.13, 204.15, 128/204.17, 203.26, 203.27; 165/140, 141, DIG. 10; 261/DIG. 65, 104

[56] References Cited

U.S. PATENT DOCUMENTS

| | | | |
|---|---|---|---|
| 1,123,201 | 12/1914 | Almirall | 165/140 |
| 2,670,933 | 3/1954 | Bay | 165/140 |
| 3,871,373 | 3/1975 | Jackson | 128/203.27 |
| 4,010,748 | 3/1977 | Dobritz | 128/203.27 |
| 4,146,597 | 3/1979 | Eckstein et al. | 128/204.13 |
| 4,150,671 | 4/1979 | Tiger | 128/201.13 |
| 4,155,961 | 5/1979 | Benthin | 128/204.13 |

*Primary Examiner*—Henry J. Recla
*Attorney, Agent, or Firm*—McGlew and Tuttle

[57] ABSTRACT

The humidity exchanger for a breathing apparatus and a conduit for the passage of inspiration and expiration air comprises a housing having an opening at each end and with a bundle of fiber tubules extending longitudinally through the housing and embedded at respective ends in packing so as to define a space within the housing around the tubes. Inspiration air is directed upwardly through the tubes past a non-return valve and out through a fitting which also forms a passage for the expiration air. The fitting also extends in communication with an inlet for the tube chamber, the space in the housing around the tubes and between the packing. An outlet is also provided for the chamber around the tubes which extends out to atmosphere.

10 Claims, 2 Drawing Figures

HUMIDITY EXCHANGER FOR A BREATHING APPARATUS

FIELD AND BACKGROUND OF THE INVENTION

This invention relates in general to respirating devices and in particular to a new and useful breathing apparatus humidity exchanger.

In breathing apparatus it must be ensured that the air passages of the patient do not dry out and that his heat balance is not disturbed. This risk exists particularly when the cold inspiration air is supplied to the patient through a tracheotomy tubule or through an intratracheal catheter. In these cases the rhino-pharingeal area, which normally humidifies and warms up the inspiration air, is bypassed.

In order to prevent drying and cooling, it is known to provide a ventilating air humidifier, which brings the inspiration air to a value of more than 70% relative humidity, and approximately to room temperature.

Subdivided according to the principal design, ventilating air humidifiers with humidification of the ventilating air from a water supply and by a humidity exchange from the humidified expiration air into the relatively dry inspiration air are known.

In a ventilating air humidifier with a water supply, the ventilating air is fed to the patient from an air supply through a corrugated hose. Inside this hose is arranged a folded water-carrying hose, which is connected with its connections to the water supply. The wall of the water-carrying hose is waterproof, but is permeable to water vapor. The ventilating air is conducted through the corrugated hose which surrounds the water carrying hose. It is humidified by the water passing through in vapor form. In a further development, the hose carrying the ventilating gas can be arranged in a water bag hanging around the neck of the user and connected into the ventilating gas connection to the respirator or directly from the atmosphere to the user. The ventilating hose with polytetrafluoroethylene walls extending can be a part of the water bag. Its inlet can be connected either directly to the atmosphere or to a portable container with liquid oxygen. Its outlet leads to tracheotomy tubule or to a nose catheter. It is indicated that the water supply is heated by the body heat.

A disadvantage is the relatively large water supply, whose temperature must be controlled and whose large volume close to the patient always represents a potential risk when the water supply runs out. Adequate humidification of the ventilating air or of the ventilating gas requires larger diameters for the ventilating air guide. These known ventilating air humidifers are therefore very large. Heating the inspiration air by the body temperature over the water supply is also problematic (U.S. Pat. No. 3,871,373).

Another known ventilating air humidifier for respirators with humidification from a water supply also contains a waterproof foil, which is permeable to water vapor, however, and which is charged on one side with water, while the ventilating gas to be humidified passes by on the other side charged with gas. The object of arranging the evaporation surface in a star form is to achieve a greater evaporative power. In order to further reduce the size of the ventilating air humidifier without reducing the evaporation surface and thus the evaporative power, the water vapor permeable foil is formed in a patent of addition by the walls of hollow fibers. The hollow fibers are arranged as a bundle parallel to each other in a housing. They are secured together with water-carrying and a water discharge pipe on the end faces in a packing. The water to be evaporated is supplied and discharged through the water carrying pipes. It wets the hollow fibers.

This ventilating air humidifier also depends on a relatively large water supply. The heating requires special measures (West German Patent No. 4,010,748, with the additional West German Pat. No. 2,617,985 which corresponds to U.S. Pat. No. 4,146,597).

In a known humidity exchanger in apparatus for ventilation and anesthesia, where the humidity contained in the ventilating air is separated and the separated water is evaporated into the inspiration air, the inspiration and expiration channels conducted in counterflow have a diffusion foil as a common partition so that the water contained in the expiration air in vapor form can get through the diffusion foil into the inspiration air by diffusion. In order to prevent the heat contained in the expiration air from escaping into the surrounding atmosphere, the humidity exchanger can be surrounded by a heat insulation.

Humidity exchangers of this type are very large. A sufficient water vapor passage requires a corresponding large foil surface in long inspiration and expiration channels. In order to heat the inspiration air sufficiently, the heat insulation must insulate these channels well from the atmosphere (see West German Offenlegungsschrift No. 25 29 050).

SUMMARY OF THE INVENTION

The present invention comprises a humidity exchanger in a respirator with a special consideration of the application to tracheometized users, which requires no water supply, ensures the heating of the inspiration air, and is small and light-weight.

In accordance with the invention there is provided a humidity exchanger which comprises a bundle of tubules arranged in a housing and defining flow passages therethrough for inspiration air which passes through the tubes of the housing and to a non-return valve which opens during inspiration. During expiration the return valve closes and expiration air flows through the fitting of one side of the housing into an opening to the housing which is in the space surrounding the tubes between packing arranged at each end of the housing through which the tubes pass. In this manner the expiration air is used to control both the humidity and temperature of the incoming inspiration air.

Accordingly, it is an object of the invention to provide a device for use with respirators which includes a housing having a bundle of tubules which is connected therethrough a non-return valve and a fitting so that inspiration air may be directed through the tubules and expiration air may be directed through the fitting into a chamber surrounding the tubules for humidifying and warming the incoming inspiration air.

A further object of the invention is to provide a humidifier for respirators which is simple in design, rugged in construction and economical to manufacture.

The decisive advantages of the invention includes a much larger evaporation surface, which can be accommodated in a small space. This permits the transfer of the humidity of the expiration air into the inspiration air. There is no additional water supply. Due to the compact arrangement, the heat energy is stored in the hollow fibers and heats the inspiration air during inspiration. The necessary heat transfer into the inspiration air is not hindered by the thin walls of the hollow fibers. The flow resistance is extremely low, due to great numbers of fibers. The inspiration air and/or expiration air can be conducted both through the hollow fibers and through the space around the hollow fibers.

The humidity exchanger, which is simple in design, permits a construction of the exchange body as a disposable article.

Advantageous developments are where exhaled micro-organisms do not multiply, despite favorable living conditions, or are even killed completely.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
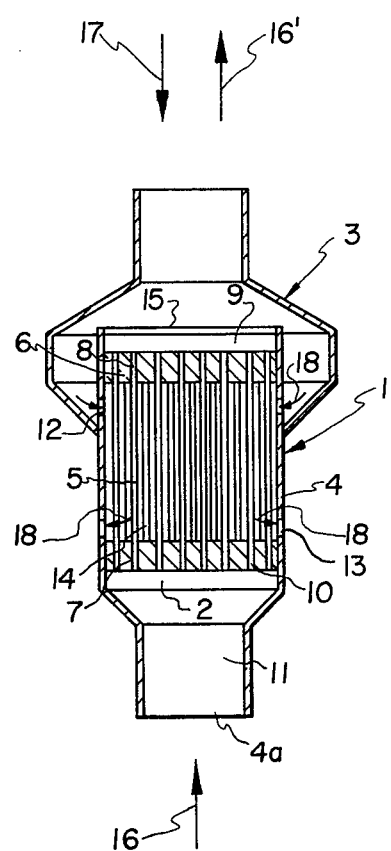
FIG. 1 is an axial sectional view of a humidity exchanger constructed in accordance with the invention.

Referring to the drawings, in particular the invention embodied therein, in FIG. 1 comprises a humidity exchanger generally designated 1 which comprises a housing 4 having an opening 4a for the inflow of inspiration air in a direction of the arrow indicated 16. The housing 4 defines an exchange body 2 which includes packing 6 and 7 at spaced axial locations therealong through which a bundle of tubules or tubes 5 of a fiber material capable of transferring both heat and humidity through the walls thereof extend. The housing 4 also includes a space 14 around the tubes and between the packing 6 and 7 within the housing which provides an exchange chamber for the transfer of humidity and heat to the inspiration air. The inspiration air 16 moves out of the housing 4 through a passage of a connection piece 3 to a patient for breathing by the patient as indicated by the arrow 16'. When the patient breathes out expiration air it flows in the direction of the arrow 17 through the connecting piece 3 and because a non-return valve 15 is closed it flows around the ends of the housing 4 and through an inlet opening 12 into the space 14 and then out through an outlet opening 13 to the atmosphere. The non-return valve 15 is set to open during inspiration to permit inflow of the inspiration air through the tubules and then in the direction of the arrow 16' and to close once inspiration stops and expiration air directed in the direction of the arrow 17 into the space 14.

A humidity exchanger 1 according to FIG. 1 comprises an exchange body 2 with a first connecting piece 3. The first connecting piece 3 can be held on an elongated inner housing 4 by means of tight fit to permit removal of the exchange body 2. In the bore of the inner housing 4, hollow fibers 5 are held parallel to each other as a bundle in axially spaced packings 6 and 7. The top hollow fiber openings 8 point to front outflow chamber 9, the bottom hollow fiber openings 10 to an inflow chamber or connection opening 11.

Inner housing 4 has on the inside, close to packing 6, top opening 12 and close to packing 8 bottom openings 13. Top opening 12 connect space 14 around hollow fibers 5, between the packings 7, 8 and within the housing 4, with the interior compartment of the first connecting piece. The bottom openings 13 connect space 14 with the surrounding atmosphere. Front outflow chambers 9 is terminated by non-return valve 15 opening away from it into the interior of the first connecting piece 3.

On the outer and inner surface or only on the outer surface of hollow fibers 5 is applied copper and/or silver by vacuum evaporation. These metals can also be applied by cathode sputtering.

Humidity exchanger 1 works as follows:

The dry and cold inspiration air 16 is conducted over opening 11 through hollow fibers 5, and after non-return valve 15 has opened, through the first connecting piece 3 to the patient. During its passage through hollow fibers 5, it has absorbed heat stored from expiration air 17 in the hollow fiber walls and the humidity transported through the hollow fiber walls. Because of the closed non-return valve 15 expiration air 17 flows over the interior of the first connecting piece 3 through top openings 12 in the direction of arrows 18 through space 14, and through bottom openings 13 into the surrounding atmosphere.

Figure 2:
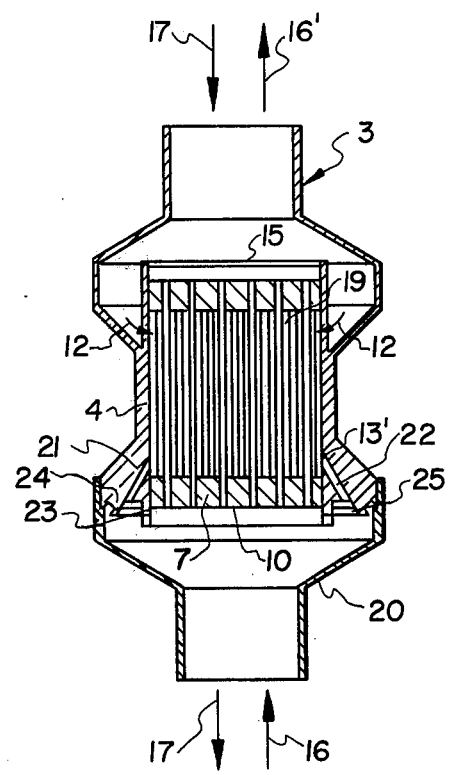
FIG. 2 is a view similar to FIG. 1 of another embodiment of the invention.

Humidity exchanger 19 according to FIG. 2 had additionally a second connecting piece 20. It is secured on a reinforcement 21 of inner housing 4. Bottom openings 13' extend as channels 22 to end face 23. They terminate inside a ring-shaped crater 24 of ring-shaped non-return valve 25 which overlies the crater. It opens away from end face 23 into the interior of the second connecting piece 20.

The mode of operation of humidity exchanger 19 is the same as that of humidity exchange 1. But the inspiration air 16, as well as the expiration air 17 are supplied and discharged through the first and second connecting pieces 3 and 20. The inspiration air 16 to be humidified and heated can thus flow, as desired, either through the interior of hollow fibers 5 or through space 14 around hollow fibers 5; the expiration air flows the other way.

A suitable hollow fiber consists of a thin permeable diaphragm, which is carried by a supporting construction. The thickness of the diaphragm of the order of a few micron, it depends on the requirement of the permeation; the thickness of the supporting construction depends on the mechanical load.

While specific embodiments of the invention have been shown and described in detail to illustrate the application of the principles of the invention, it will be understood that the invention may be embodied otherwise without departing from such principles.

What is claimed is:

1. A humidity exchanger for a breathing apparatus comprising an elongated housing having a bore extending therethrough for passing one of inspiration air and expiration air from an inlet opening to an outlet opening, axially spaced packings adjacent said inlet opening and said outlet opening dividing said housing into an inflow chamber and an outflow chamber and a tubule bank chamber therebetween, a bundle of fiber tubules in said tubule bank chamber, each of said fiber tubules having opposite ends extending through said axially spaced packings to define flow passages therethrough from said inflow chamber to said outflow chamber and a space around the exteriors of said tubules between said packing and within said housing, said tubules being made of a material permeable to humidity, a first connection piece mounted to said housing about said outlet opening to define an outlet compartment therebetween, said housing having means for directing the other of said one of inspiration air and expiration air from said outlet compartment to and through said space and along the exterior of said tubules in indirect heat exchange and humidity exchange with said one of inspiration air and expiration air in said flow passages and from said space to atmosphere, and non-return valve means mounted to said outlet opening for selectively opening a path from said outflow chamber for passing said one of inspiration air and expiration air from said flow passages and closing said outflow chamber for preventing the passage of the other of said inspiration and expiration air to said flow pasasges.

2. A humidity exchanger as set forth in claim 1, wherein said directing means includes channels extending in the wall of said housing adjacent said inlet opening from said space, said channels having a ring-shaped crater at the end thereof, and a ring-shaped non-return valve mounted to said housing and overlying said crater operative for passing air from said space out through said channel to atmosphere and preventing the backflow passage of air from atmosphere through said channel to said space.

3. A humidity exchanger as set forth in claim 2, including copper on the outer and inner surfaces of said tubules.

4. A humidity exchanger as set forth in claim 2, including copper on the outer surfaces of said tubules.

5. A humidity exchanger, as set forth in claim 3 or 4, wherein said copper is deposited on said tubules by vacuum evaporation.

6. A humidity exchanger as set forth in claim 3 or 4, wherein said copper is deposited in said tubules by cathode sputtering.

7. A humidity exchanger as set forth in claim 2, including silver on the outer and inner surfaces of said tubules.

8. A humidity exchanger as set forth in claim 2, including silver on the outer surfaces of said tubules.

9. A humidity exchanger, as set forth in claim 7 or 8, wherein said silver is deposited on said tubules by vacuum evaporation.

10. A humidity exchanger as set forth in claim 7 or 8, wherein said silver is deposited on said tubules by cathode sputtering.

* * * * *